United States Patent [19]

Münch et al.

[11] Patent Number: 5,453,283

[45] Date of Patent: Sep. 26, 1995

[54] ORALLY ADMINISTERED SOLVENT-FREE PHARMACEUTICAL PREPARATION WITH DELAYED ACTIVE-SUBSTANCE RELEASE, AND A METHOD OF PREPARING THE PREPARATION

[75] Inventors: Ulrich Münch; Hans-Jürgen Mika; Bernhard Emschermann; Rainer Schmidt; Bernhard Sczepanik, all of Bundesrepublik, Germany

[73] Assignee: Schwarz Pharma AG, Bundesrepublik, Germany

[21] Appl. No.: 30,437

[22] PCT Filed: Oct. 7, 1991

[86] PCT No.: PCT/DE91/00791

§ 371 Date: Apr. 7, 1993

§ 102(e) Date: Apr. 7, 1993

[87] PCT Pub. No.: WO92/05774

PCT Pub. Date: Apr. 16, 1992

[51] Int. Cl.⁶ ............................................. A61K 9/14
[52] U.S. Cl. .......................... 424/489; 424/488; 424/490
[58] Field of Search ................................. 424/490, 489, 424/488, 455; 514/398, 520, 413

[56] References Cited

U.S. PATENT DOCUMENTS

| 5,213,808 | 5/1993 | Bar-Shalom et al. | 424/488 |
| 5,246,714 | 9/1993 | Dahlinder et al. | 424/489 |
| 5,262,173 | 11/1993 | Sheth et al. | 424/489 |

*Primary Examiner*—Thurman K. Page
*Assistant Examiner*—William E. Benston, Jr.
*Attorney, Agent, or Firm*—Kane, Dalsimer, Sullivan, Kurucz, Levy, Eisele and Richard

[57] ABSTRACT

Delayed release pharmaceutical preparations include a solvent free, solidified melt granulate of a pharmaceutical ingredient in admixture with a meltable auxiliary substance which is soluble in the pharmaceutical ingredient at elevated temperatures.

13 Claims, No Drawings

ORALLY ADMINISTERED SOLVENT-FREE PHARMACEUTICAL PREPARATION WITH DELAYED ACTIVE-SUBSTANCE RELEASE, AND A METHOD OF PREPARING THE PREPARATION

BACKGROUND OF THE INVENTION

1. Field of the Invention

The invention relates to a solventless, orally administered pharmaceutical preparation with a delayed active substance release and method for making same, without using any solvents.

2. Brief Description of Related Art

A number of possibilities for making oral slow release drugs are known in the pharmaceutical technology. Different galenic principles are used. The active substance may be modified or diffusion barriers may be erected. In particular the latter principle is very often used in the current practice. The active substance is coated with polymer systems or the drug is bound into matrix systems, from which it is then released. Thereby, mainly organic solvents are used.

Common solvents are used, for example, chlorinated hydrocarbons, in particular methyl chloride, acetone or alcohol.

They will be needed to dissolve the given slow release matrix forming auxiliary agent as well as to coat or bond the remaining auxiliary agents. Furthermore they are used as a wetting agent for granulation purposes.

While hitherto, the reaching of certain goals were in the foreground when developing retarding preparations namely, among others, maintaining therapeutic plasma concentrations by avoiding active fluctuations over a long period of times;

Avoidance of too high plasma concentration peaks, so as to reduce undesirable effects;

Extend the dosaging interval for obtaining an improved patient compliance. The interest now is directed to be able to make slow release preparations without the use of solvents while obtaining the aforementioned goals.

On account of changed environmental considerations there is now a demand of being able to make drugs without the use of solvents. Official regulations for disposing of the solvents used and in particular the avoidance of toxicological risks of the solvent residue amounts in the drug formulations, for example, chlorinated hydrocarbons, require one not to use solvents when making slow release types of drugs.

Furthermore, in the meantime, it had been shown that within the category of "oral types of drugs", (Multiple Unit Dosage Forms) have advantages over monolithic form of drugs (Single Units). In particular, from the pharmaceutical point of view, unit dosage forms are preferred over single units. For example, multiple-unit preparations have shorter stomach passage times and permit a rapid and uniform distribution of the defined subunits over the total gastrointestinal tract. Thus local irritations can be avoided due to high drug concentrations. At the same time, the danger of a "dose dumping" is reduced. The fluctuations of the AUC-values and the scatterings of the relevant target dimensions lag time $C_{max}$ and $t_{max}$ are lower.

However, the making of multiple type of slow release drugs in accordance with the hitherto manufacturing methods by using solvents still results in risks for the proper pharmaceutical quality of the preparations. The reproducability of a good pharmaceutical quality within one charge (charge homogenity) as well as from charge to charge (charge conformity) is not always assured, (H. Blume, Biopharmaz. Aspekte von Multiple Unit Dosage Forms, 1988).

Although, a whole series of forms of drugs are known for the long time dispensation of active substances, there is still a further need for improved forms of drugs.

SUMMARY OF THE INVENTION

It is an object of the present invention to provide an orally administered pharmaceutical preparation with a delayed active substance release without any solvent residue amounts contained therein, which can be further processed into multiple forms of drugs (multiple unit dosage forms), or in form of monolithic drugs (single units). Furthermore, it is an object of the invention to provide methods for making such a pharmaceutical preparation with a delayed active substance release, which exlude the use of solvents.

Simultaneously, the amount of the used active substance should be varied in wide limits by maintaining a good pharmaceutical active substance, and the release of the active substance should be controllable in a targeted manner.

This object is solved in that the pharmaceutical preparation is free from solvents and consists of cooled down granulated melt, at least a molten active substance and at least an auxiliary substance.

DETAILED DESCRIPTION OF THE INVENTION

The molten active substance is used as the solvent for at least one auxiliary agent which dissolves while effecting the slow release. Thus, the active substance melt is the solvent for the auxiliary agent. Both together enable the wet granulation for forming a slow release matrix.

In the pharmaceutical preparation, in accordance with the invention all pharmacological active substances may be used as active substances, which do not decompose in the melt and which dissolve the auxiliary substances totally or partially.

As forms of drugs, solid dispensing drugs may be considered, like pellets, capsules, granula and dragees. Pellets and the granula which is pressed into quickly breaking up parts of tablets are suitable in the most advantageous manner. These forms are subjected to a reproducible kinetic movement in the stomach-intestinal tract. The transit time from leaving the stomach until reaching the colon is well predictable and independent from food intake (S.S. Davis et al., Int. J. Pharmaceutics, 21, 331–340 (1984). Typically. it is 3–4 hrs. (J.C. Hardy, J.Nucl. Med., 25,59 (1984).

Drug forms of the preparation in accordance with the invention are characterized in that they can be adjusted in a simple manner to the given requirements of the active substance release, known to the person skilled in that art.

In one embodiment of the invention the active substance is isosorbiddinitrate.

In accordance with a further embodiment the active substance is isosorbid-5-mononitrate (5-ISM).

Preferably thermoplasts are used as the matrix forming auxiliary agents.

Preferably, the used auxiliary agents are a combination of polyvinyl acetate and highly dispersed silicon-dioxide (Aerosil). The form of the drug is a tablet, a pellet, a capsule or a dragee. The pharmaceutic preparation in accordance with the invention may be made in that a mixture consisting of at least one active substance and at least one auxiliary substance is molten, until a homogenic uniformly wetted through mass is kneaded and subsequently granulated.

The pharmaceutical preparation in accordance with the invention may also be made by melt extrusion.

The invention will be described in detail in the following. By changing the quantity ratio of active substance used,or an active substance mixture and auxalliary agent or auxiliary agents or a variation of the ratio of mass to the surface of the blanks may define the characteristics of the pharmaceutical preparation.

The use of water insoluble substances, like talcum or highly dispersed silicon dioxide in combination with the water insoluble matrix former, for example, polyvinylacetate (PVA) results in a stable matrix skeleton.

The skeleton provides a structure stability and keeps the pores of the matrix open. The viscosity is reduced.

Additions of water soluble substances, like lactose, increase the porosity and thereby the release speed of the active substance. Talcum as a mechanical obstacle prolongs the diffusion paths and results in a slowing down of the active substance release. The mass in the heated condition, consisting of molten active substance and the dissolved auxiliary agents therein, is kneadable and deformable,so that a complete homogenic mixture or "wetting" can be achieved. At a lower temperature, in particular body temperature, a complete stability of the structure is provided. This stability is maintained in the presence of water or simulated digestive juices.

In view of the thermoplastic behavior which is present at a high temperature,the method of melt extrusion may be used for making the mixture.

Exemplified embodiment 1

2.5 g of an ISDN/lactose mixture, consisting of 40% ISDN and 60% lactose were dry mixed with 0.7 sifted off fine component of polyvinylacetate (commercial type Vinapas B 5 spezial) and 0.6 g highly dispersed silicon dioxide (Aerosil 200 were sifted through a tea sifter, heated in a drying oven to about 80° C. and kneaded with the pestle until a homogenic uniformly wetted through viscous mass was generated. During the cooling off a trace of ISDN/lactose-mixture 40/60 was scattered over it for seeding and kneaded with the pestle. The crystallisation during kneading reulted to a solid material in a short time, which slowly further hardened. It behaved somewhat plastic, but also did easily break. Small pieces were rolled out into thin strands on a heated metal plate at 40° to 50° C. and were cut into small pieces after hardening Next day the pieces were fed through a 1-mm-sieve. The fine component was sifted off with the tea sieve.

Table 1

Table I shows the in-vitro-active substance release of nonpressed blanks at pH 1.2 and a constant temperature of 37° C.+/−1° C. in dependency from the time, corresponding to the agitator blade method, in accordance with the European drug book (Ph. Eur.). 800 ml artificial stomach juice pH 1.2 were made from 2 g NaCl with 0.1 n HCl ad l—1 as the test liquid. The mixing speed was 120 Rpm.

Results:

In vitro-testing of the nonpressed blanks for release:

| Time | Active substance not pressed (Percentage of the total content) |
| --- | --- |
| after 1 hr | 34.9% |
| after 2 hrs | 50.1% |
| after 4 hrs | 68.2% |
| after 6 hrs | 78.6% |

These release results show the suitability of the blanks for processing into multiple unit dosage forms, for example, capsules.

Exemplified embodiment 2

Making of pellets and processing into rapidly breaking up tablets. 2.5 g of an ISDN/Lactose-mixture,consisting of 40% ISDN and 60% lactose were dry mixed with 0.7 g sifted off fine component polyvinylacetate (commercial type Vinapas B 5 spezial) and 0.6 g highly dispersed silicon dioxide (Aerosil 200 ), sifted through a tea sieve and in a mortar heated in a drying oven at about 80° C., kneaded with the pestle until a homogenic uniformly wetted through viscose mass was obtained. During the cooling off a trace of ISDN/lactose-mixture 40/60 was scattered over it for seeding and kneaded with the pestle. The crystallisation during kneading resulted in a solid material in a short time, which slowly further hardened. It behaved somewhat plastic,but also easily broke. Small pieces were rolled out into thin strands on a heated metal plate at 40° to 50° C. and were cut into small pieces after hardening and fed through a 1 mm sieve. Further additives which are customary for making tablets were added to the pellets. Subsequently the tablets were made with a pressure force of 2 t.

Table 2

Table 2 shows the in-vitro-active substance release of tablets at pH 1.2 and a constant temperature of 370° C.+/−1° C. In dependency from the time, in accordance with the agitator blade method, according to the European drug book (Ph. Eur). 800 ml artificial stomach juice pH 1.2 were made from 2 g NaCl with 0.1 n HCl ad 1 l, as the test liquid. The mixing speed was 120 rpm.

Release:

In vitro testing of the tablets for release:

| Time | Active agent released (Percentage of the total content) |
| --- | --- |
| after 1 hr | 35.8% |
| after 2 hrs | 51.0% |
| after 4 hrs | 69.1% |
| after 6 hrs | 80.0% |

Exemplified embodiment 3

Making of the solvent free pharmaceutical preparation in accordance with the melt extrusion method and processing into matrix tablets. 2.5 kg ISDN/lactose mixture, composed of 40% ISDN and 60% lactose were admixed with sifted off fine component of 2.75 kg talcum, 0.11 kg magnesium stearate, 6.35 kg lactose, 0.75 kg poly-vinylacetate and 0.025 iron oxide,and again sifted through a 3 mm sieve. Subsequently, the mixture was placed into a double screw melt extruder, wherein it was kneaded under heat in zones of increasing temperatures from 600° to 100° C., into an homogenic uniformly wetted through viscose mass. The ejected cooled off strand was processed into thin chips. They were sifted through a Prewitt-sieve 1.25 mm. The obtained granulate was pressed into tablets with a pressure force of 2 t.

Table 3

Table 3 shows the in-vitro-active substance release in accordance with the tablets made in accordance with the exemplified embodiment 3, at pH 1.2 and a constant temperature of 1° C. in dependency from the time, in accordance with the apparatus III of USP XX S. 959.

800 ml artificial stomach juice pH 1.2 were made from 2 g NaCl with 0.1 n HCl ad 1 l, as the test liquid. The stroke frequency of the apparatus III was 30/sec.

Results:

In-vitro testing of the granulate which were pressed into tablets:

| Time | Active substance released (Percentage of the total-content) |
|---|---|
| after 2 hrs | 46.0% |
| after 4 hrs | 64.2% |
| after 6 hrs | 77.2% |

We claim:

1. A pharmaceutical preparation for oral administration with a delayed release of the active ingredient which consists of a solvent free, solidified melt granulate, having dispersed therein a meltable melted active ingredient; and a meltable auxiliary substance which is soluble in the active ingredient.

2. The preparation in accordance with claim 1, wherein the active ingredient is isosorbiddinitrate.

3. The preparation in accordance with claim 1, wherein the active ingredient is isosorbide-5-mononitrate.

4. The preparation in accordance with claim 1 wherein said auxiliary substance is a thermoplastic other than wax.

5. The preparation in accordance with claim 1 wherein said auxiliary substance is polyvinylacetate.

6. The preparation in accordance with claim 1 which further comprises a structure former selected from the group consisting of silicon dioxide, lactose and talcum.

7. A pharmaceutical preparation with a delayed release of the active ingredient which consists of a solvent free, solidified melt granulate, a meltable melted active ingredient, a meltable auxiliary substance which is soluble in the active ingredient at an elevated temperature, and a structure former.

8. The preparation in accordance with claim 7, wherein the active ingredient is isosorbiddinitrate.

9. The preparation in accordance with claim 7, wherein the active ingredient is isosorbide-5-mononitrate.

10. The preparation in accordance with claims 7–9, wherein said auxiliary substance is a non-wax thermoplastic.

11. The preparation in accordance with claims 7–10, wherein said auxiliary substance is polyvinylacetate.

12. The preparation in accordance with claims 7–11, wherein the structure former is selected from the group consisting of a highly disperse silicon dioxide, lactose and talcum.

13. The preparation in accordance with claims 7–12, wherein the form of the medication is selected from the group consisting of a tablet, a pellet, a capsule or a dragee.

* * * * *